United States Patent [19]

Voorhies

[11] 4,194,506
[45] Mar. 25, 1980

[54] KIT FOR AN OSTOMATE

[76] Inventor: Paul A. Voorhies, 1517 Gardenia Dr., Metairie, La. 70005

[21] Appl. No.: 853,919

[22] Filed: Nov. 22, 1977

[51] Int. Cl.² ............................................. A61F 5/44
[52] U.S. Cl. ..................................................... 128/283
[58] Field of Search ........... 134/168, 167, 172, 166 R; 128/225, 227, 230, 283; 239/589, 536; 206/223, 581

[56] References Cited

U.S. PATENT DOCUMENTS

| | | | |
|---|---|---|---|
| 466,680 | 1/1892 | Harris | 134/166 R |
| 1,272,263 | 7/1918 | Hooker | 239/586 |
| 1,521,892 | 1/1925 | Koppin | 128/227 UX |
| 1,687,012 | 10/1928 | Forth | 134/166 X |
| 1,754,708 | 4/1930 | Bevins | 239/589 |
| 1,940,615 | 12/1933 | Webster | 128/187 R |
| 2,223,566 | 12/1940 | Koch | 134/44 |
| 2,283,700 | 5/1942 | Ahern | 134/168 R |
| 2,438,073 | 3/1948 | Saur | 128/283 |
| 2,540,777 | 2/1951 | Deahl | 128/283 |
| 2,607,622 | 8/1952 | Doepke | 239/530 X |
| 2,869,547 | 1/1959 | Yohe | 128/283 |
| 3,042,312 | 7/1962 | Packards | 239/315 |
| 3,042,315 | 7/1962 | Besser | 239/530 |
| 3,618,606 | 11/1971 | Brown et al. | 128/283 |

FOREIGN PATENT DOCUMENTS 662475  5/1963  Canada ..................................... 128/283

*Primary Examiner*—Robert W. Michell
*Assistant Examiner*—Milford Juten
*Attorney, Agent, or Firm*—David H. Semmes; Warren E. Olsen

[57] ABSTRACT

An improved kit for an ostomate, comprising a drainable stoma bag appliance of the type consisting of a flexible, vertically elongated member with a closed top end for attachment to the stoma of the patient, with a downwardly open bottom end that is openable for flushing. The present invention comprises such a stoma bag appliance together with a novel directional water flushing appliance consisting essentially of a hand-operated positive shut-off valve member for actuating a water outlet tube which is a rigid J-shaped tubular conduit, with a distal end including a directional spray orifice. With the present kit, an ostomate may greatly facilitate directional flushing of the stoma bag, since the ostomate can manipulate a directional flushing action to selected portions of the interior of the stoma bag, without danger that the seal between the stoma bag and the stoma of the patient will be broken.

5 Claims, 3 Drawing Figures

KIT FOR AN OSTOMATE

BACKGROUND OF THE INVENTION

1. Field of the Invention

The present invention relates to an improved kit for an ostomate, i.e., a person who has undergone the medical procedure of inserting a stoma within his or her abdomen, to shunt the direction of excrement for direct discharge through the stoma bag appliance. One who has undergone an ileostom or colostoma operation is required to cleanse the interior of his appliance whenever it becomes partly filled with excrement, normally several times a day. The present invention is directed to the kit in combination with a drainable stoma bag appliance of the type which includes an orifice for sealing connection to the stoma of the ostomate, and particularly a seal which is developed by a Karaya ring. There exists a need for a flushing device which will allow the ostomate to cleanse the interior of his appliance without subjecting the Karaya ring to direct water pressure, which could break the seal of the appliance against the abdomen of the ostomate.

2. Description of the Prior Art:

The following prior U.S. Pat. Nos. are known to applicant, and considered pertinent to the examination of this application:

Harris—466,680
Hooker—1,272,263
Forth—1,687,012
Koch—2,223,566
Saur—2,438,073
Deahl—2,540,777
Yohe—2,869,547
Packard—3,042,312

The present invention constitutes significant improvement over any of the teachings of these prior art patents in that none of these patents are in recognition of the peculiar problems presented to an ostomate, and the combination of structure which is presented as a solution herein. The present invention allows selective control over a flushing operation, through one-hand manipulation of a directional water flushing appliance. The present invention requires no separate inlets or outlets to be applied to an ostomy bag, rather with the present kit the ostomate employs a drainable conventional stoma bag appliance and is able to easily manipulate the water flushing appliance to the available bottom end of the stoma bag.

Saur, U.S. Pat. No. 2,438,073, illustrates a colostomy bag having a flushing distributor that includes a header with a plurality of holes permanently mounted within the bag, as shown most clearly in FIG. 3. His distributor employs an external pipe connection, and it is manifestly clear that Saur's device is inapplicable to a drainable stoma bag appliance of the type simply consisting of a flexible vertically elongated member, in major contrast to the approach taken in the present invention.

Deahl, U.S. Pat. No. 2,540,777, shows a colostomy appliance having another form of integral and separate flushing connection, through a fixture on the bag itself. As Deahl illustrates in FIG. 2, the hose is connected to an integral fitting, which is itself attached rigidly to the bag construction. Deahl's device is also not concerned with allowing a complete manipulation of the directional water spray onto all surfaces of the bag interior, since he is primarily concerned with an irrigation function of the stoma.

Yohe, U.S. Pat. No. 2,869,547, illustrates a colostomy irrigating structure, and one which also requires separate orifices in the stoma bag itself. For flushing purposes, the Yohe device requires a separate inlet on the upper surface, for the insertion of a water bulb, all as shown in FIG. 2.

Koch, U.S. Pat. No. 2,223,566, illustrates another colostomy irrigating device, one which requires structural interconnections of water supplies into various portions of the bag itself. The colostomy bag of Koch is again a special adaptation of structure, in complete distinction to the concept taught herein which allows the use of a conventional stoma bag appliance.

Packard, U.S. Pat. No. 3,042,312, illustrates a known form of spraying device, which is hand-operated with a positive shutoff valve member. As such, Packard illustrates that such a type of valve member is, of course, well known.

Forth, U.S. Pat. No. 1,687,012, as well as Harris, U.S. Pat. No. 466,680, illustrate bottle washing devices, wherein a U-shaped pipe is inserted into the downwardly open end of a vessel, such as a milk bottle, and fixedly mounted therein to apply a spray to the interior of the vessel. Of course, none of these patents are analogous to the particular combination presented herein, and furthermore neither of these teachings are in recognition of the peculiar problems involved in the flushing of a drainable stoma bag appliance. Furthermore, neither of these structural solutions are manipulatable for a selected directional flushing of the interior of the vessel.

Finally, Hooker, U.S. Pat. No. 1,272,263, illustrates a plurality of orifices located at the distal end of a U-shaped conduit. Hooker's teaching is specific to a gas burner, which is completely non-analogous to the present teaching which allows an ostomate to efficiently perform a necessary daily maintenance.

SUMMARY OF THE INVENTION

The present invention relates to an improved kit which allows an ostomate to quickly and accurately discharge accumulated excrement through a conventional stoma bag appliance. The improved kit consists of a drainable stoma bag appliance which is of the simplest conventional type of construction, consisting of a flexible, vertically elongated member having a closed top end that is sealingly connected to the stoma, or abdomen opening of the ostomate. The drainable stoma bag appliance also includes a bottom end, which is downwardly openable and conventionally closed by folding over the downwardly open end, and attaching a clip or other sort of closure. For purposes of illustration, one form of such a drainable stoma bag is manufactured by Hollister, Inc., of Chicago, Ill. with an overall length of approximately 12 inches, with a Karaya seal ring of an approximately 1½ inch diameter. The Karaya ring acts to seal the orifice of the stoma bag against the abdomen of the ostomate, and conventionally the ring is also held in its sealed position through the provision of a belt worn around the waist of the ostomate, and connected to a plastic attachment proximate the Karaya ring.

The second major element of the improved kit taught herein is the directional water flushing appliance, comprising a hand-operated positive shut-off valve member which is connected at its outlet to a rigid J-shaped tubular conduit. The short leg of the J enables the ostomate to control a valve without danger that the valve, or his hand, will be in contact with the effluent which is flushed downwardly by gravity during the operation. The distal end of the long leg of the J-shaped tube includes a directional spray orifice, which can be manipulated against desired interior surfaces of the stoma bag appliance with great accuracy.

Accordingly, it is a major feature of the present invention to provide an improved kit for an ostomate, enabling him to perform the necessary flushing action of a stoma bag with reduced danger that the Karaya ring seal will be damaged by the flushing action.

It is a significant related feature of the present invention that the improved kit taught herein has as one of its major elements a conventional drainable stoma bag, since the present invention allows the ostomate to perform his maintenance without requiring expensive, specially adapted elongated stoma bags as has heretofore been the practice shown by the representative prior art, discussed above.

Other advantages and features of the present invention will become more apparent from the detailed description which follows, wherein reference is made to the accompanying figures.

Figure 1:
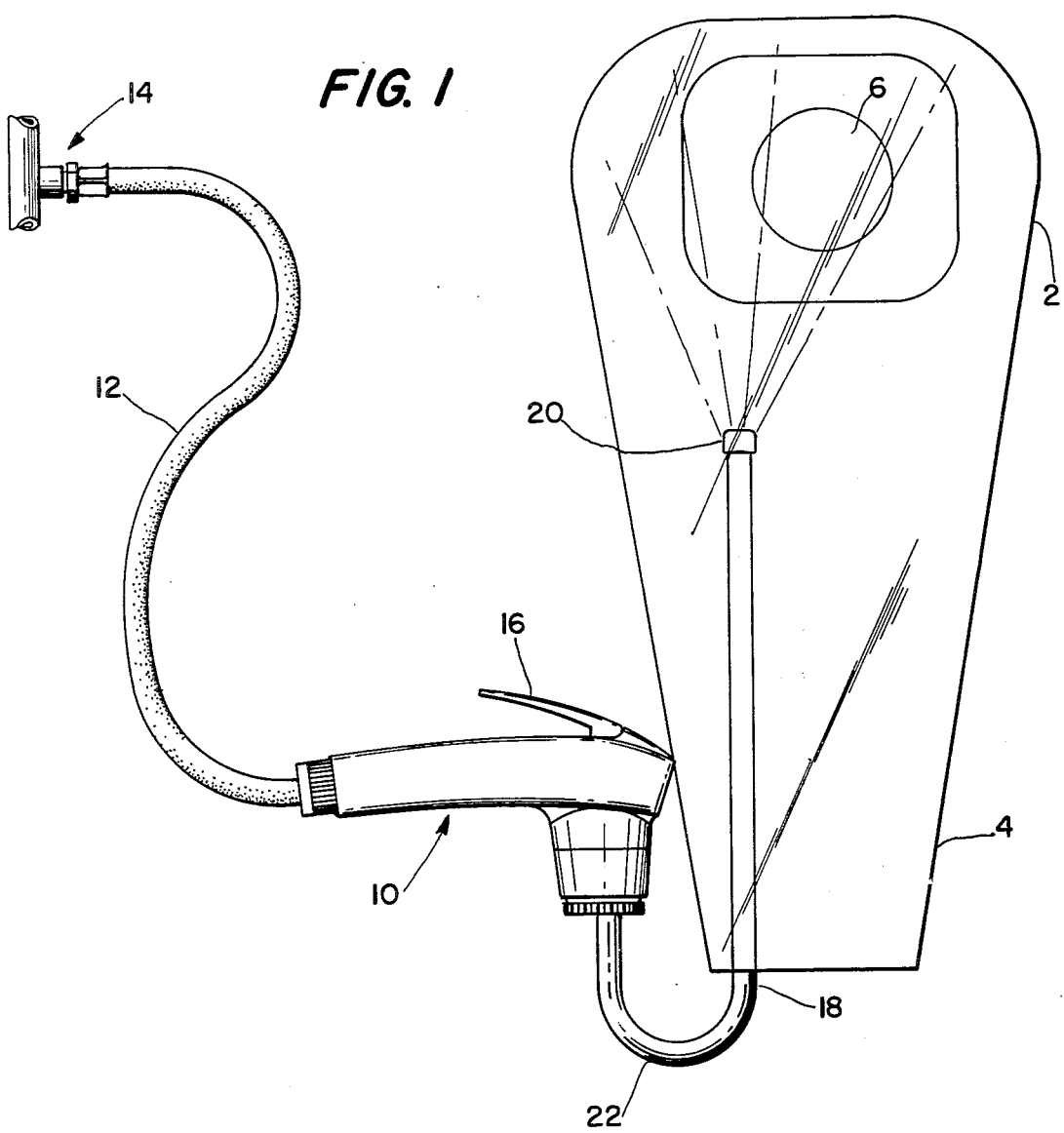
FIG. 1 is a front view, schematically showing a preferred embodiment of the present invention.

The preferred embodiment of the invention is shown in FIG. 1. A drainable stoma bag appliance, 2, conventionally consisting of a flexible vertically elongated member has a closed top end, with an orifice, 6, for sealing connection to the stoma of the ostomate. A drainable stoma bag such as model no. 7223, manufactured by Hollister Co., Inc., of Chicago, Ill., has an orifice of 1½ inch diameter, with a Karaya seal at the location, 6, together with attachments for a belt to be worn around the abdomen of the ostomate. This representative drainable stoma bag is approximately 12 inches in length in the vertical direction, and is constructed of a transparent flexible plastic.

Figure 2:
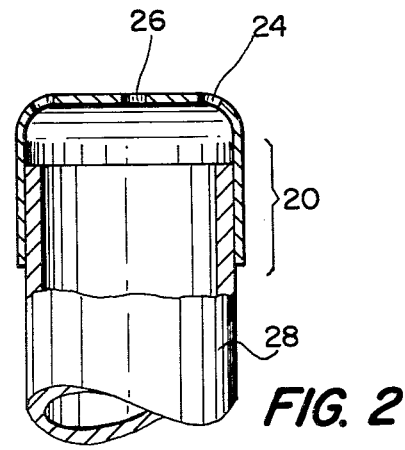
FIG. 2 is a partial sectional view of the distal end of the J-shaped tube.
Figure 3:
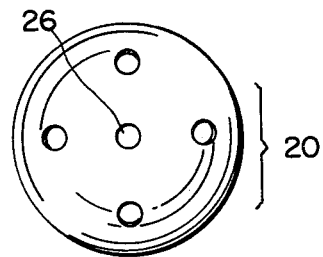
FIG. 3 is a top view showing the orifice arrangement in the preferred embodiment of the invention.

The second element of this invention is the directional water flushing appliance, 10, which comprises a hand-operated positive shut-off valve member which in the preferred embodiment is actuated by a thumb-operated operating lever, 16. The valve member is connected, at its inlet end, to a flexible supply conduit, 12, which is adapted by any conventional means, 14, to a household water source. The outlet end of the valve member is connected to a rigid J-shaped tubular conduit, the short leg, 22, ending at a proximate end which is directly attached to the outlet of the valve member, 10. The long leg thereof, 18, extends to a distal end, 20, which includes at least one spray orifice adapted to issue a directional water spray therefrom. Accordingly, the ostomate is enabled to insert the long leg upwardly into the downwardly open end of the stoma bag, 4, and manipulate a directional flushing action to selected portions of the interior of the stoma bag appliance. In the preferred embodiment, the long leg of the J-shape rigid tube is substantially equal to the vertical distance between the top and bottom ends of the stoma bag appliance, so that the directional flushing action issuing from the distal end, 20, can be most accurately applied to desired interior portions of the stoma bag. In the preferred embodiment the thumb-operated lever, 16, will be horizontally disposed on an upper surface of the valve member, 10, when the long leg of the water outlet tube is so vertically disposed within the stoma bag appliance. This facilitates manipulation by the ostomate, since the valve member in his hand will be out of the path of the water and excrement being discharged through the downwardly open end of the stoma bag appliance, 4. It has been found that the J-shaped tube can be preferably constructed of a rigid tubing, such as metal or plastic, having approximately a ¼ inch inner diameter, with a distal end of the tube including a thin-walled cap. As illustrated in FIG. 2, the distal end of the tubing, 28, is totally encircled by the thin wall cap, 24, and the cap includes a plurality of orifices, 26, arranged to direct the water spray substantially in a direction colinear with the center line of the longer leg of the rigid tubing.

The kit taught by the present invention enables the user to accurately control both the amount of water dispensed, through operation of the thumb-lever, and the direction of its flow. The present invention does not require any modification or specially constructed form of drainable stoma bag, since the ostomate simply takes the downwardly open end of the stoma bag, 4; removes the closure, not shown; and inserts the long leg of the J-shaped tube vertically upward with a flushing abrasion. Normally, the ostomate will be sitting on a water closet, or standing facing such a depository, bending at the knees. Due to the proximity between the distal end of the J-shaped tube, and the stoma at 6, the ostomate may be able to carefully clean the stoma region, without permitting inadvertent water pressure to destroy the Karaya ring seal of the appliance against the abdomen of the ostomate. The present invention allows the ostomate to maintain a cleaner stoma, a cleaner interior surface of the stoma bag appliance, resulting in longer intervals required between complete changes of the drainable bag.

Various changes may be made in the invention without departing from the scope thereof, and the present invention is to be defined solely by the scope of the appended claims.

I claim:

1. An improved kit for an ostomate, comprising, in combination:

A. a drainable stoma bag appliance of the type consisting of a flexible, vertically elongated, member having a closed top end, which includes an orifice with a sealing ring means for sealing connection of said orifice about the stoma of the ostomate, and a bottom end, which is downwardly open and adapted for a closure means to close said open end; and B. a directional water flushing appliance, comprising a hand-operated positive shut-off valve member which is connected, at an inlet end, to a means for supplying water pressure, and at an outlet end to a directional water outlet tube; wherein, C. said water outlet tube consists of a rigid J-shaped tubular conduit, the short leg thereof ending at a proximate end which is attached to said valve outlet and the long leg thereof being substantially equal to the vertical distance between the top and bottom ends of said stoma bag appliance and ending at a distal end which includes at least one spray orifice adapted to issue a directional water spray therefrom, in a direction substantially colinear to said long leg, whereby the ostomate is enabled to insert said long leg upwardly within the downwardly open end of said stoma bag appliance and manipulate a directional flushing action to selective portions of the interior of said stoma bag.

2. The combination according to claim 1 wherein the means for supplying water pressure comprises a flexible supply conduit adapted for connection to a household water source, and said valve member further comprises a thumb-operated operating lever.

3. The combination according to claim 2 wherein said thumb-operated lever is horizontally disposed on an upper surface of said valve member when the long leg of said water outlet tube is vertically disposed within said stoma bag appliance.

4. The combination according to claim 1 wherein the water outlet tube consists of a round tubing of approximately ¼ inch inner diameter, with the distal end including a thin-walled cap having a plurality of spray orifices arranged to direct a water spray substantially in a direction colinear with the centerline of said longer leg.

5. The combination according to claim 4 wherein said J-shaped water outlet tube is approximately 12 inches in length, with said short leg approximately 2 inches in length and said long leg approximately 10 inches in length.

* * * * *